US010143721B2

(12) United States Patent
O'Keefe et al.

(10) Patent No.: US 10,143,721 B2
(45) Date of Patent: Dec. 4, 2018

(54) COMBINATION PRODUCT FOR THE PREVENTION OF SEXUALLY TRANSMITTED INFECTIONS

(71) Applicants: THE POPULATION COUNCIL, INC., New York, NY (US); THE UNITED STATES OF AMERICA, AS REPRESENTED BY THE SECRETARY, DEPT. OF HEALTH AND HUMAN SERVICES, Washington, DC (US)

(72) Inventors: Barry R. O'Keefe, Frederick, MD (US); Melissa Robbiani, New York, NY (US); José A. Fernández Romero, Bronx, NY (US)

(73) Assignees: The Population Council, Inc., New York, NY (US); The United States of America, as represented by the Secretary, Dept. of Health and Human Services, Washington, DC (US)

( * ) Notice: Subject to any disclaimer, the term of this patent is extended or adjusted under 35 U.S.C. 154(b) by 0 days.

(21) Appl. No.: 15/114,505

(22) PCT Filed: Jan. 13, 2015

(86) PCT No.: PCT/US2015/011197
§ 371 (c)(1),
(2) Date: Jul. 27, 2016

(87) PCT Pub. No.: WO2015/116375
PCT Pub. Date: Aug. 6, 2015

(65) Prior Publication Data
US 2016/0339076 A1   Nov. 24, 2016

Related U.S. Application Data

(60) Provisional application No. 61/932,706, filed on Jan. 28, 2014.

(51) Int. Cl.
| | | |
|---|---|---|
| *A01N 37/18* | (2006.01) |
| *A61K 38/00* | (2006.01) |
| *A61P 31/18* | (2006.01) |
| *A61K 38/16* | (2006.01) |
| *A61K 9/06* | (2006.01) |
| *A61K 45/06* | (2006.01) |
| *A61K 31/717* | (2006.01) |
| *A61K 31/731* | (2006.01) |
| *A61K 33/04* | (2006.01) |
| *A61K 33/30* | (2006.01) |
| *A61K 33/34* | (2006.01) |
| *A61K 36/04* | (2006.01) |
| *A61K 47/12* | (2006.01) |
| *A61K 47/14* | (2017.01) |

(52) U.S. Cl.
CPC ............. *A61K 38/16* (2013.01); *A61K 9/06* (2013.01); *A61K 31/717* (2013.01); *A61K 31/731* (2013.01); *A61K 33/04* (2013.01); *A61K 33/30* (2013.01); *A61K 33/34* (2013.01); *A61K 36/04* (2013.01); *A61K 38/168* (2013.01); *A61K 45/06* (2013.01); *A61K 47/12* (2013.01); *A61K 47/14* (2013.01)

(58) Field of Classification Search
CPC . A61K 2300/00; A61K 31/731; A61K 38/168
See application file for complete search history.

(56) References Cited

U.S. PATENT DOCUMENTS

| | | | |
|---|---|---|---|
| 8,088,729 B2 | 1/2012 | O'Keefe et al. | |
| 8,367,098 B2 | 2/2013 | Maguire et al. | |
| 2009/0099149 A1* | 4/2009 | Liu | A61K 9/006 514/182 |
| 2010/0256089 A1 | 10/2010 | Maguire et al. | |

FOREIGN PATENT DOCUMENTS

| | | |
|---|---|---|
| WO | 94/15624 A1 | 7/1994 |
| WO | 0195951 A1 | 12/2001 |
| WO | 03093322 A2 | 11/2003 |
| WO | 2006071102 A1 | 7/2006 |
| WO | 2007064844 A2 | 6/2007 |

OTHER PUBLICATIONS

Karnchanatat, Antimicrobial Agents, Antimicrobial Activity of Lectins from Plants, Aug. 23, 2012, pp. 145-178.*
Emau et al., J. Med. Primatol., 2007, 36, 244-253.*
Levendosky et al., Antimicrobial Agents and Chemotherapy, Dec. 2015 vol. 59 No. 12, p. 7290-7298.*
McGowan, Current Opinion HIV AIDS, Rectal microbicides, 2012, pp. 1-8.*
Contraceptive Sponge, Family Practice Notebook, available online at: http://fpnotebook.com/Gyn/Contraception/CntrcptvSpng.htm, accessed on May 20, 2017.*
Acetic acid, from http://www.newworldencyclopedia.org/entry/Acetic_acid, accessed on Sep. 22, 2017.*
Sodium acetate, from http://www.softschools.com/formulas/chemistry/sodium_acetate_formula/383/, accessed on Sep. 22, 2017.*
Nelega, Natural Wellbeing Distribution Inc., Jun. 15, 2012.*

(Continued)

*Primary Examiner* — Rachael E Bredefeld
*Assistant Examiner* — Kaipeen E Yang
(74) *Attorney, Agent, or Firm* — Lerner, David, Littenberg, Krumholz & Mentlik, LLP

(57) ABSTRACT

Disclosed are compositions for inhibiting transmission of a sexually transmitted infection that contain one or more polyanionic microbicides, such as carrageenans, including lambda carrageenan, as well as water-soluble metal salts and specified lectins. Also disclosed are methods for making and using the compositions.

15 Claims, 3 Drawing Sheets

(56) References Cited

OTHER PUBLICATIONS

Just Right by Purina, https://www.justrightpetfood.com/zinc-sulfate, accessed on Sep. 22, 2017.*
Shah et al., African Journal of Biotechnology, vol. 8 (9), pp. 1959-1964, May, 4, 2009.*
International Search Report and Written Opinion for Application No. PCT/US2015/011197 dated Mar. 30, 2015.
International Written Opinion for Application No. PCT/US2015/011197 dated Jan. 11, 2016.
Buck, Christopher B., et al., Carrageenan Is a Potent Inhibitor of Papillomavirus Infection, PLoS Pathogens, Jul. 2006, vol. 2, Issue 7, e69, pp. 1-10.
Tanaka, Haruo, et al., Mechanism by which the lectin actinohivin blocks HIV infection of target cells, PNAS, Sep. 15, 2009, vol. 106, No. 37, 15633-15638.
O'Keefe, Barry R. et al., Scaleable manufacture of HIV-1 entry inhibitor griffithsin and validation of its safety and efficacy as a topical microbicide component, PNAS, Apr. 14, 2009, vol. 106, No. 15, 6099-6104.
Massai, Rebeca, et al., Vaginal rings for contraception in lactating women, Steroids, 65 (2000), 703-707.
Kumar, Narender, et al., Nestorone®: a progestin with a unique pharmacological profile, Steroids, 65, (2000), 629-636.
Odlind, Viveca, et al., Unaltered Lipoprotein and Carbohydrate Metabolism during Treatment with Contraceptive Subdermal Implants Containing ST-1435, Upsala Journal of Medical Sci 89: 151-158, 1984.
Nixon, et al., Griffithsin Protects Mice from Genital Herpes by Preventing Cell-to-Cell Spread, Journal of Virology, Doi:10.1128/JVI.00012-13, 2013, pp. 1-39.
Dana Huskens and Dominique Schols, Algal Lectins as Potential HIV Microbicide Candidates, Marine Drugs, 2012, 10, 1476-1497; doi:10.3390/md10071476.
W. Sergio, Zinc Salts that may be Effective Against the AIDS Virus HIV, Medical Hypotheses, (1988), 26, 251-251.
Ting-Chao Chou, Theoretical Basis, Experimental Design, and Computerized Simulation of Synergism and Antagonism in Drug Combination Studies, Pharmacological Reviews, Copyright 2006, The American Society for Pharmacology and Experimental Therapeutics, 58:621-681, 2006.
Brichacek, Beda, et al., In Vivo Evaluation of Safety and Toxicity of a Lactobacillus jensenii Producing Modified Cyanovirin-N in a Rhesus Macaque Vaginal Challenge Model, PLOS ONE, Nov. 2013, vol. 8, Issue 11, pp. 1-8.
Takebe, Yutaka, et al., Antiviral Lectins from Red and Blue-Green Algae Show Potent In Vitro and In Vivo Activity against Hepatitis C Virus, PLOS ONE, May 2013, vol. 8, Issue 5, pp. 1-10.
Lahteenmaki, Pertti L.A.., et al., Milk and Plasma Concentrations of the Progestin St-1435 in Women Treated Parenterally With ST-1435, Contraception, Nov. 1990, vol. 42, No. 5, pp. 555-562.
Romano, Joseph W., et al., Non-Specific Microbicide Product Development: Then and Now, Current HIV Research, 2012, vol. 10, No. 1, pp. 1-10.
Rupp, Richard, et al., VivaGel™ (SPL7013 Gel): A candidate dendrimer—microbicide for the prevention of HIV and HSV infection, International Journal of Nanomedicine 2007:2(4) 561-566.
Fenstermacher, Katherine J. and Destefano, Jeffrey, Mechanism of HIV Reverse Transcriptase Inhibition by Zinc, Journal of Biological Chemistry, Nov. 25, 2011, vol. 286, No. 47, pp. 40433-40442.
Trkola, Alexandra, et al., A Cell Line-Based Neutralization Assay for Primary Human Immunodeficiency Virus Type 1 Isolates That Use either the CCRS or the CXCR4 Coreceptor, Journal of Virology, Nov. 1999, p. 8966-8974.
McCormack, Sheena, et al., PRO2000 vaginal gel for prevention of HIV-1 infection (Microbicides Development Programme 301): a phase 3, randomised, double-blind, parallel-group trial, Lancet 2010, 376; 1329-37.
Ann Robbins and C. Wayne Bardin, Nestorone™ Progestin the Ideal Progestin for Use in Controlled Release Delivery Systems, Annals New York Academy of Sciences, 1997, pp. 38-46.
Fernandez-Romero, Jose A., et al., Zinc Acetate/Carrageenan Gels Exhibit Potent Activity In Vivo against High-Dose Herpes Simplex Virus 2 Vaginal and Rectal Challenge, Antimicrobial Agents and Chemotherapy, p. 358-368, 2011.
Kenney, Jessica, et al., A Modified Zinc Acetate Gel, a Potential Nonantiretroviral Microbicide, Is Safe and Effective against Simian-Human Immunodeficiency Virus and Herpes Simplex Virus 2 Infection In Vivo, Antimicrobial Agents and Chemotherapy, Aug. 2013, vol. 57, No. 8, p. 4001-4009.
Haraguchi, Yugi, et al., Inhibition of HIV-1 infection by zinc group metal compounds, Antiviral Research 43 (1999) 123-133.
Huang, Chaobo, et al., Electrospun cellulose acetate phthalate fibers for semen induced anti-HIV vaginal drug delivery, Biomaterials, 33 (2012) 962-969.
Lennette et al., Diagnostic Procedures for Viral, Rickettsial, and Chlamydial Infections, Edition 7, revised, American Public Health Association, 1995, pp. 142-143.

* cited by examiner

COMBINATION PRODUCT FOR THE PREVENTION OF SEXUALLY TRANSMITTED INFECTIONS

CROSS-REFERENCE TO RELATED APPLICATIONS

The present application is a national phase entry under 35 U.S.C. § 371 of International Application No. PCT/US2015/011197 filed Jan. 13, 2015, published as WO 2015/116375 A1, which claims priority from U.S. Provisional Patent Application No. 61/932,706 filed Jan. 28, 2014, all of which are incorporated herein by reference.

BACKGROUND OF THE INVENTION

There is a worldwide unmet need for technologies that simultaneously protect against human immunodeficiency virus (HIV) and other sexually transmitted infections (STIs). Microbicides that concurrently protect against HIV and other STIs would address these health risks in an acceptable and affordable manner, and make a major contribution to public health globally. Also, a microbicide that has indications against STIs other than HIV may make use of such microbicide more acceptable to those not as concerned about HIV and thereby increase acceptability and adherence.

Unfortunately, previous studies with single active pharmaceutical ingredients (APIs) with broad anti-viral activity and ability to block different STIs in vitro or in vivo have not shown efficacy in clinical trials. The reasons for such lack of efficacy in clinical trials are unknown, but may be due to a variety of reasons, including e.g., low potency, short window of protection, reduction of activity in the presence of biological fluids, or induction of mucosal and microflora changes. Romano, J. W., et al., *Non-specific microbicide product development: then and now*. Current HIV research, 2012. 10(1): p. 9-18. Thus, there is a continuing need to identify more potent and safe APIs which may be used alone or in combination for microbicidal use.

Compounds with known in vivo microbicidal activity include the carrageenans. Carrageenans are polysaccharides which may be obtained from the red algae commonly known as seaweed. They are a structural component of seaweed and are extracted as three main types, namely iota, kappa and lambda, although there are other types as well, including kappa-II, mu and nu carrageenans. Carrageenans have been used extensively in the food, pharmaceutical, and cosmetics industries as thickeners, gelling agents, and stabilizing and dispersing agents. Extensive pharmacological and toxicological studies have been conducted. Carrageenan has been found to be non-toxic by oral, dermal, and inhalation routes of administrations even at extremely high doses. The carrageenans were therefore classified as "generally recognized as safe" (GRAS) by the FDA in 1972. Food and Drug Administration. GRAS (Generally recognized as safe) food ingredients: Carrageenan. FDA Publications PB-221 206, (1972).

Further extensive oral pharmacokinetic studies conducted in pigs, rats, mice, gerbils, guinea pigs, ferrets, hamsters, dogs, and monkeys showed that the breakdown of the carrageenans in the gastrointestinal tract was minimal at best and that absorption was virtually non-existent. Benitz, K. F., et al., *Toxicol. Appi. Pharmacol.* 22, 282 (1972); Fox, M. R. S. & Jacobs, R. M. Metal Ions in Biological Systems, pp. 214-248 (Marcel Decker, Inc., 1986); Luscombe, D. K. & Nicholls, P. J. *Fd. Cosmet. Toxicol.* 11, 229-237 (1973); Naess, B. Acta Vet. Scand. 12, 592-600. 1971; Samman, S. & Roberts, D. C. K., *Med. J. Australia* 146, 246-249 (1987); U.S.EPA. Health Effects Assessment of for Zinc (and Compounds). EPA/540-1-96-048. 1984. Washington, D.C., US Environmental Protection Agency, Office of Research and Development; Walden, J. T. & Derreth, D. FDA New Release 72/55. *FDA Publications* 72/55, (1972); Walker, A. P. et al. *Fd. Chem. Toxic.* 35, 1099-1106 (1997); Weiner, M. L. Intestinal transport of some macromolecules in food. *Fd. Chem. Toxic.* 26, 10, 867-880 (1988).

International Patent Publication WO 94/15624 teaches use of sulfated polysaccharides such as iota carrageenan, dextran sulfate, kappa carrageenan, lambda carrageenan, heparin mimetics, heparin sulfate, pentosan polysulfate, chondrotin sulfate, lentinan sulfate, curdlan sulfate, de-N-sulfated heparin and fucoidan, to inhibit cell-to-cell transmission of HIV and thus the sexual transmission of Acquired Immune Deficiency Syndrome (AIDS), as well as *Chlamydia* organism. This publication teaches that iota carrageenan is the most efficacious of the commercially available sulfated carrageenans in preventing HIV infection and in blocking *Chlamydia* infection in vitro and in vivo.

Zinc is another known inhibitor of such sexually transmitted pathogens as HIV and Herpes simplex virus 2 (HSV-2). Zinc acetate (ZA) and zinc sulfate have been shown to inhibit HIV infection in cell culture, and HSV-2 in both cell culture and laboratory animals. Zinc salts have been shown to be effective in blocking infection by HIV in vitro (Haraguchi, Y., et al. *Antiviral Res* 43, 123-133 (1999)) and also blocking infection by foot-and-mouth virus, human rhinovirus, influenza A and B, semliki forest virus and sindbis virus. Sergio, W. *Medical Hypotheses* 26, 253 (1988). Haraguchi, et al. found that zinc chloride, cadmium acetate and mercury chloride inhibited HIV-1 production as assayed by p24 ELISA and RT. Zinc chloride did not exhibit significant cytotoxicity when present in concentrations of up to 550 µg/mL.

Lectins are carbohydrate binding proteins which may have roles in the immune system by binding to carbohydrates present on invading pathogens. The lectin known as Griffithsin (GFRT or G) has been reported to have potent anti-HIV activity, and can block HIV replication in vitro at subnanomolar concentrations ($IC_{50}$ values 0.02 to 0.8 nM). See Alexandre, K. B., et al., Virology, 2012. 423(2): p. 175-86; Huskens, D. and D. Schols, Marine Drugs, 2012, 10(7): p. 1476-97; Mori, T., et al., The Journal of biological chemistry, 2005. 280(10): p. 9345-53; and also U.S. Pat. No. 8,088,729, the contents of all of which are incorporated by reference herein in their entirety.

Griffithsin can be produced in multigram quantities in tobacco plants. O'Keefe, B. R., et al., Proceedings of the National Academy of Sciences of the United States of America, 2009. 106(15): p. 6099-104. Notably, GRFT resists degradation by several proteases, is highly stable even at high temperatures, is non-irritating, does not induce cellular activation, and induces only minimal changes in secretion of inflammatory cytokines and chemokines by blood or epithelial cells. O'Keefe, B. R., et al., Proceedings of the National Academy of Sciences of the United States of America, 2009. 106(15): p. 6099-104; Kouokam, J. C., et al., PloS one, 2011. 6(8): p. e22635; Moncla, B. J., et al., Advances in bioscience and biotechnology, 2011. 2(6): p. 404-408.

Griffithsin has shown excellent safety and efficacy against HIV in explant models, and modified forms of GRFT have been reported as having improved potency, stability, and solubility. O'Keefe, B. R., et al., Proceedings of the National Academy of Sciences of the United States of America, 2009.

106(15): p. 6099-104. GRFT also has been shown to have in vivo activity against HSV-2. Nixon, B., et al., Journal of virology, 2013. 87(11): p. 6257-69.

Applicants have previously reported that a complex between a water-soluble metal salt and carrageenans can provide anti-microbial effects. The water-soluble metal salt can be a zinc metal, and in a particular embodiment, a combination of zinc acetate (ZA) formulated in a carrageenan gel has been shown to be active against HIV, HSV-2, human papillomavirus (HPV), and *T. vaginalis*. Fernandez-Romero, J. A., et al., Antimicrobial agents and chemotherapy, 2012. 56(1): p. 358-68; Kenney, J., et al., Antimicrobial Agents and Chemotherapy, 2013. 57(8): p. 4001-9. See also, U.S. Pat. No. 8,567,098 the entire contents of which are incorporated by reference herein. Notwithstanding, the need for additional broad spectrum, more potent microbicides which can protect against HIV and/or other STIs still exists.

SUMMARY OF THE INVENTION

Applicants have discovered that microbicidal compositions with broad and extremely potent activity may be produced by combining lectins with a water-soluble metal salt and/or carrageenans. Accordingly, in a first aspect the present invention is directed to an antimicrobial composition comprising an effective amount of an antimicrobial agent comprising one or more lectins and one or more additional antimicrobial agents selected from the group consisting of a physiologically acceptable water soluble metal salt, carrageenan, or other polymers like dendrimers, cellulose, cellulose analogues, cellulose derivatives, and combinations thereof.

In a particular embodiment the composition comprises one or more lectins in combination with a zinc metal salt (Z) and/or a carrageenan (C). In particular embodiments, the antimicrobial compositions of the present invention can comprise the lectin Griffithsin in combination with a zinc metal salt (GZ); or may comprise Griffithsin in combination with carrageenans (GC); or may comprise Griffithsin in combination with a zinc metal salt and carrageenans (GZC). In various particular embodiments the zinc metal salt is zinc acetate (ZA) and/or the carrageenan.

In additional embodiments, the compositions of the invention may be in any physical form suitable for delivery of the antimicrobial agents, including as a gel, or in solution, or as a solid, or in dried or powdered forms.

In a related aspect, the present invention is directed to a sexually transmitted infection (STI) inhibiting composition comprising an antimicrobial composition of the present invention. As contemplated herein, the composition may prevent vaginal or rectal transmission of STIs, and is formulated accordingly.

The compositions of the present invention may further include one or more additional antimicrobial agent, and/or a drug, including but not limited to a vaginally or rectally administrable drug, to provide a composition which may be administered to a subject to treat or prevent one or more conditions as a multipurpose prevention technology.

It is understood herein that prevention of other conditions in addition to microbial infections are envisioned herein. For example, in a particular embodiment, the compositions may comprise one or more anti-microbial agents and may further comprise a hormonal or non-hormonal anti-contraceptive agent to prevent unintended pregnancy, or may include an agent for hormone replacement therapy.

As contemplated herein, in a further aspect the compositions of the present invention may be pharmaceutical compositions and thus further comprise one or more antimicrobial agents or drugs disclosed herein in addition to one or more pharmaceutically acceptable agents or excipients. In a particular embodiment, the composition is formulated as an over-the-counter pharmaceutical composition. In a particular embodiment, the pharmaceutically acceptable agent or excipient is a physiologically acceptable pH controlling agent and/or a physiologically acceptable preservative. In another embodiment, the pharmaceutically acceptable agent or excipient facilitates delivery of the pharmaceutical composition to a subject in need thereof. In particular embodiments, the pharmaceutical composition is formulated in a dosage form suitable for vaginal and/or rectal administration.

In a further aspect, the invention is directed to methods of inhibiting microbial infection in a subject in need thereof comprising administering to the subject an effective amount of an anti-microbial composition of the present invention. Thus, in one embodiment, the method comprises administering an anti-microbial composition comprising an effective amount of GRFT and carrageenan to a subject in need thereof in order to inhibit infection by HPV.

In another embodiment, the method comprises administering an anti-microbial composition comprising an effective amount of GRFT and a zinc metal salt to a subject in need thereof in order to inhibit infection by HIV. In a particular embodiment the zinc metal salt is ZA.

In another embodiment, the method comprises administering an anti-microbial composition comprising an effective amount of GRFT, carrageenan, and a zinc metal salt to a subject in need thereof in order to inhibit infection by HSV-2.

In another embodiment, the method comprises administering an anti-microbial composition comprising an effective amount of GRFT, Carrageenan, and a zinc metal salt to a subject in need thereof in order to inhibit infection by one or more of HIV, HSV-2, HPV, and other sexually transmitted infections (STIs).

In a further embodiment, the method comprises administering an anti-microbial composition comprising an effective amount of GRFT to a subject in need thereof in order to inhibit infection by HPV. In a particular embodiment, the composition further comprises carrageenan.

DESCRIPTION OF THE DRAWINGS

In FIG. 1A, anti-HIV activity was tested in TZM-bl cells using the MAGI assay (RBegay O, et al. AIDS Research and Human Retroviruses, 2011 Sep. 1; 27(9):1019-24) and the laboratory strains HIV-1$_{MN}$ (X4 virus) and HIV-1$_{ADA-M}$ (R5 virus). In FIG. 1B, anti-HIV activity was tested in PBMC (Trkola A, et al., J Virol. 1999 November; 73(11):8966-74) using the laboratory strains HIV-1$_{NL4-3}$. In FIG. 1C, anti-HPV activity was evaluated in HeLa cells using a luciferase reporter gene assay (Buck C B, et al. PLoS Pathog. 2006 Jul. 1; 2(7):e69) and testing the antiviral activity against three different HPV PsV types (16, 18 and 45). In FIGS. 1A, 1B, 1C, IC$_{50}$ values are depicted as a vertical dotted line with the 95% confidence interval and were calculated using a dose-response-inhibition analysis on GraphPad Prism v5.0 software. All the non-toxic GRFT concentrations were tested in triplicates and are shown with the mean±SD.

FIG. 2A depicts inhibition of virus adsorption. The plaque inhibition assay was performed as previously described. Ashley, R., Herpes simplex viruses, p 375-395. In Schmidt N J, Emmons R W (ed), Diagnostic procedures for viral, rickettsial, and chlamydial infections, 7th ed. American Public Health Association, Washington, D.C. 1995. HSV-G strain and different concentrations of GRFT or media (virus control) were pre-incubated for 0, 0.5, 1 and 2 h at 37° C. before adding to pre-chilled Vero cells and kept at 4° C. The monolayers were washed three times with cold media before adding a methylcellulose overlay and incubated for 48 h at 37° C., 5% $CO_2$ and 98% humidity before fixing, staining and counting the plaque forming units (pfu). The % of virus replication was calculated versus the virus control. FIG. 2B depicts inhibition of virus entry. The same assay was performed as in FIG. 2A but after the 2 h incubation at 4° C., the cells were switched to 37° C., 5% $CO_2$ and 98% humidity for an additional 2 h. The monolayers were treated for 2 minutes with citric acid buffer (pH=3.0) to inactivate any virus remaining on the cell surface. The monolayers were washed three times with cold media before adding a methylcellulose overlay and incubated for 48 h at 37° C., 5% $CO_2$ and 98% humidity before fixing, staining and counting the plaque forming units (pfu). The graph shows % of virus replication (mean±SD) relative to virus control (triplicates per condition).

DETAILED DESCRIPTION OF THE INVENTION

Figure 1:
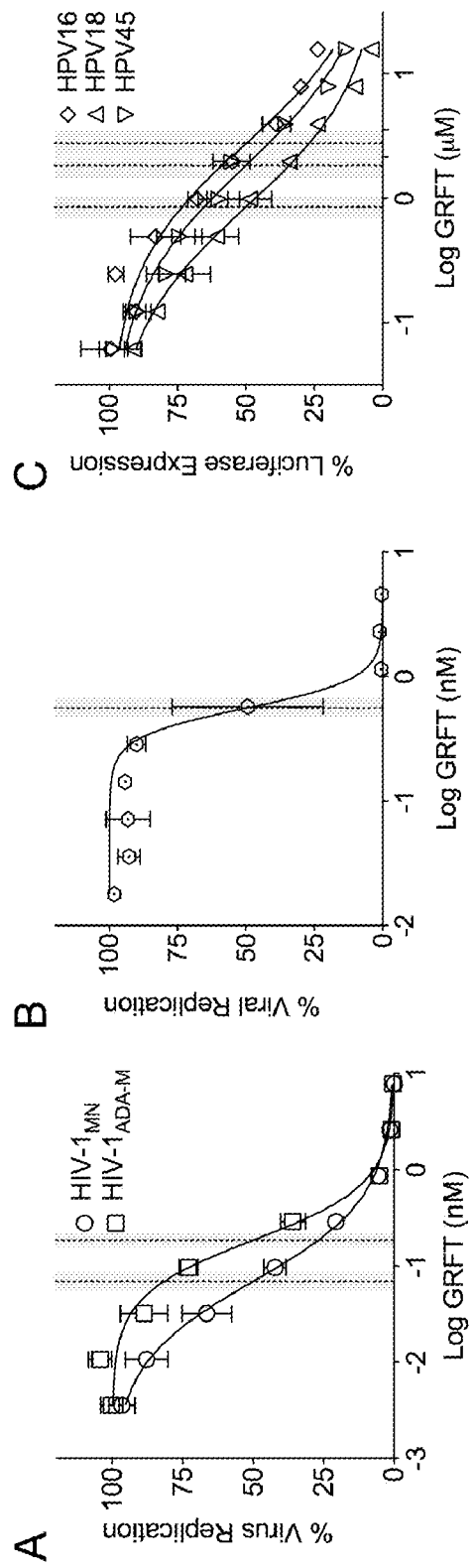
FIG. 1 includes logarithmic plots which show the percentage of virus replication in the presence of GRFT (nM). Data in FIG. 1 A and FIG. 1 B confirm that GRFT has potent activity against HIV. Data in FIG. 1 C indicate that GRFT has moderate in vitro activity against HPV16, HPV18, and HPV45 pseudoviruses (PsV).

While the specification concludes with the claims particularly pointing and distinctly claiming the invention, it is believed that the present invention will be better understood from the following description.

All percentages and ratios used herein are by weight of the total composition unless otherwise indicated herein. All measurements made are at 25° C. and normal pressure unless otherwise designated. All temperatures are in Degrees Celsius unless specified otherwise. The present invention can comprise (open ended) or consist essentially of the components of the present invention as well as other ingredients or elements described herein. As used herein, "comprising" means the elements recited, or their equivalent in structure or function, plus any other element or elements which are not recited. The terms "having" and "including" are also to be construed as open ended unless the context suggests otherwise.

All ranges recited herein include the endpoints, including those that recite a range "between" two values. Terms such as "about," "generally," "substantially," and the like are to be construed as modifying a term or value such that it is not an absolute, but does not read on the prior art. Such terms will be defined by the circumstances and the terms that they modify as those terms are understood by those of skill in the art. This includes, at very least, the degree of expected experimental error, technique error and instrument error for a given technique used to measure a value.

Unless otherwise indicated, as used herein, "a" and "an" include the plural, such that, e.g., "a carrageenan" can mean at least one carrageenan, as well as a plurality of carrageenans, i.e., more than one carrageenan, including but not limited to, carrageenans of different types.

Where used herein, the term "and/or" when used in a list of two or more items means that any one of the listed characteristics can be present, or any combination of two or more of the listed characteristics can be present. For example, if a composition is described as comprising agents A, B, and/or C, the composition can comprise A feature alone; B alone; C alone; A and B in combination; A and C in combination; B and C in combination; or A, B, and C in combination.

All references cited herein are hereby incorporated by reference in the entirety.

The anti-microbial effects of carrageenans and zinc metal, alone and in combination, e.g., in the form of zinc acetate/carrageenan gels, have been investigated. See, e.g., Fernandez-Romero, J. A., et al., Antimicrobial Agents and Chemotherapy, 2012. 56(1): p. 358-68; Kenney, J., et al., Antimicrobial Agents and Chemotherapy, 2013. 57(8): p. 4001-9; and U.S. Pat. No. 8,367,098 all incorporated by reference herein.

In addition, carbohydrate binding agents such as certain algal lectins have been reported as having anti-HIV activity. The most potent of these algal lectins is said to be Griffithsin (GFRT) which has been reported as having anti-viral activity against HIV, hepatitis C and SARS-related corona virus. Huskens, D. and D. Schols, Marine drugs, 2012. 10(7): p. 1476-97. GRFT has also recently been shown to have inhibitory effects on HSV-2. Nixon, B., et al., Journal of virology, 2013. 87(11): p. 6257-69.

Applicants have surprisingly and unexpectedly discovered that certain anti-microbial agents can be combined to produce anti-microbial compositions with more potent and synergistic inhibitory effects. Specifically, as disclosed herein, Applicants have observed that the anti-HIV activity of GRFT is enhanced in combination with zinc acetate (ZA) showing a synergistic antiviral effect on HIV. Also, GRFT in combination with ZA and CG (GZC) have enhanced in vitro and in vivo anti-HSV-2 activity. In addition, Applicants have also discovered that GRFT in combination with carrageenan produces a synergistic inhibitory effect on HPV.

As understood herein, the compositions of the instant invention may be formulated in a gel form such as provided herein in Example 1. As used herein, a gel, e.g., a "carrageenan gel" refers to a relatively viscous form of composition which can be used to administer the antimicrobial agents in a manner which facilitates the delivery of the composition with minimal leakage upon delivery e.g., for intravaginal or rectal administration. The compositions of the invention may be in other physical forms familiar to one of skill in the art, including but not limited to solids, solutions, or dried or powdered forms which may be particularly suitable depending on the contemplated dosage form. Thus, formulations other than gels are specifically contemplated herein, and may be made according to conventional methods. For example, the components of a composition comprising GFRT, carrageenan, and a water soluble metal salt such as zinc acetate may be combined in solution to make a composition or may be combined as a dried or powdered form by one of skill in the art using conventional laboratory techniques Applicants also report herein that GRFT alone can produce an inhibitory effect on HPV. To Applicants knowledge, this is the first time GRFT, a lectin with reported antiviral activity against envelope viruses, has been shown to have an antiviral activity against HPV, which is a naked virus.

As contemplated herein, the present invention includes anti-microbial compositions which can comprise two or more different anti-microbial agents which in combination provide enhanced inhibitory effects. It is further contemplated that such microbicidal compositions may comprise at least two different anti-microbial ingredients which can provide a synergistic effect on the anti-viral efficacy against one or more target viruses including HIV, HSV-2, HPV and other STIs. As used herein, antimicrobial agents include anti-viral agents.

"Anti-viral agents" as referred to herein are familiar to one of skill in the art. As contemplated herein, such agents include but are not limited to water soluble metal salts, including zinc metal salts, carrageenans and lectins. In addition, "anti-viral agents" include other compounds familiar to one of skill in the art including, for example, various polymers such as naphthalene sulfonates and other sulfated or sulfonated polymers (McCormack S et al., Lancet, 2010 Oct. 16; 376(9749):1329-37);

As contemplated herein, suitable microbicidal agents for use in the compositions of the instant invention (including but not limited to other anti-viral agents) are familiar to one of skill in the art. It is understood herein that these microbicidal agents include compounds which can be used against STIs including but not limited to HIV, i.e., the anti-microbials contemplated herein are not necessarily all anti-HIV microbicides. McCormack S et al., Lancet, 2010 Oct. 16; 376(9749):1329-37.

In a particular embodiment, the composition comprises ZA formulated with carrageenan in combination with GRFT or other lectin in order to produce a composition which has broad and extremely potent activity against HIV, HSV-2, HPV, and potentially other STIs. In other particular embodiments the compositions may comprise GRFT in any combination with ZA and/or a carrageenan. It is also contemplated herein that the compositions may comprise Griffithsin for use in the prevention of HPV infections.

As used herein, the term "Griffithsin" is used generically to refer to a natural Griffithsin or any related, functionally equivalent (i.e., anti-viral) polypeptide or derivative thereof, including but not limited to forms disclosed in U.S. Pat. No. 8,088,729.

As used herein, "other STIs" are familiar to one of skill in the art and include, e.g., *N. gonorrhoeae*, *C. trachomatis*, bacterial vaginosis, *T. vaginalis*, Hepatitis B and others.

Without intending to be bound by any particular theory of operation, it is believed that employing microbicides delivering different anti-microbial agents with different modes of action will likely provide compositions for more effective strategies for preventing and/or treating a broader spectrum of microbial infections, including concurrent infections by more than one pathogen, and can provide enhanced and synergistic inhibitory effect against viruses such as HIV and other STIs when one or more antimicrobial agents are employed. Thus, different antimicrobials may be combined as disclosed herein to achieve different levels of antimicrobial protection, and which upon administration in various dosage forms can be designed to last for different periods of time. It is further contemplated herein that the compositions of the present invention, being useful for preventing STIs including but not limited to HIV, will provide an anti-HIV prevention strategy which may be more acceptable for use by individuals unwilling to identify or acknowledge themselves as potentially at risk of HIV infection, and thus provide a benefit to public health worldwide.

As contemplated herein, in a particular embodiment, the anti-microbial compositions of the present invention do not include any antiretroviral drugs (ARVs). Thus, in the event that administration of a composition of the instant invention results in drug resistance, it will not be resistance against an ARV. As such, the compositions of the present invention are less likely to produce drug resistance that could compromise alternative promising treatments using ARVs. Thus, as contemplated herein use of the compositions disclosed herein avoid the selection of HIV resistant strains (which sometimes occurs upon administration of (ARVs)) and thus the compositions of the present invention provide an advantageous alternative for HIV prevention.

As contemplated herein, since the compositions of the instant invention can be used to treat concurrent infection by more than one microbe, ideally, they may be used without the need to first screen a subject for HIV. In addition, as contemplated herein, the compositions of the present invention may be formulated for over the counter (OTC) distribution. Thus, it is envisioned that the compositions will provide an increase in the accessibility and affordability of these microbicidal compositions, including anti-HIV compositions, and thus provide a significant benefit to public health.

When present in compositions of the present invention, the carrageenan includes a lambda carrageenan. To the extent that non-lambda carrageenans are present (in which the case the carrageenan component of the compositions may be referred to as "the carrageenans" or the "carrageenans mixture"), the carrageenans mixture contains at least about 50% (and preferably at least 50%) of lambda carrageenan, based on total dry weight of the carrageenans in the composition. In more preferred embodiments, the amount of lambda carrageenan is at least about 75, 76, 77, 78, 79, 80, 81, 82, 83, 84, 85, 86, 87, 88, 89, 90, 91, 92, 93, 94, 95, 96, 97, 98, or 99% of the total dry weight of the carrageenans (i.e., lambda and non-lambda carrageenans). Other preferred amounts are at least 75%, at least about 85%, at least about 95%, about 85 to about 99%, and from about 94 to about 97% lambda carrageenan. Carrageenans suitable for use in the instant invention are available from commercial vendors (e.g., Sigma Aldrich, St. Louis, Mo.)

The remainder of the carrageenans in compositions of the present invention may include at least one non-lambda carrageenan. By "non-lambda carrageenan", it is meant any carrageenan other than lambda carrageenan, such as kappa-carrageenan, iota carrageenan, kappa-II carrageenan (which contains kappa and iota carrageenans), mu carrageenan, and nu carrageenan. Non-lambda carrageenans are also available commercially (e.g., Sigma Aldrich, St. Louis, Mo.) or may be extracted from seaweed in accordance with standard techniques. In preferred embodiments, the non-lambda carrageenans include kappa carrageenan, iota carrageenan, and kappa-II carrageenans, and mixtures of any two or more thereof. In more preferred embodiments, the non-lambda carrageenan includes kappa-II carrageenan. In preferred embodiments, the non-lambda component of the carrageenans constitutes less than about 1, 2, 3, 4, 5, 6, 7, 8, 9, 10, 11, 12, 13, 14, 15, 16, 17, 18, 19, 20, 21, 22, 23, 24 or about 25% of the total dry weight of the carrageenans. In more preferred embodiments, the non-lambda component is about less than about 25%, less than about 15%, less than about 5%, about 1 to about 15%, or about 3 to about 6% of the total dry weight of the carrageenans. In other preferred embodiments, the carrageenan mixture is substantially or entirely free of dextrose, an ingredient commonly found in carrageenans used in the food industry.

Compositions containing the lambda carrageenan or the carrageenans in amounts less than 1% or greater than 5% may be used, so long as that they provide an antimicrobial effect and retain pharmaceutical acceptability, e.g., vaginal acceptability. By "vaginal acceptability", it is meant that the rheological properties such as viscosity of composition allow it to be used for its intended purpose (e.g., the composition maintains a viscosity so that it can be applied by the user and be retained in the vaginal vault, as well as providing aesthetic properties such as being substantially odorless, smoothness, clarity, colorlessness and tastelessness). The viscosity is selected so as to enable the composition to evenly coat the epithelial lining of the vaginal vault. In general, the viscosity of the compositions is about 10,000 to about 50,000 cP, preferably about 20,000 to about 50,000 cP, and more preferably about 30,000 to about 50,000 cP.

Carrageenan is a polysaccharide consisting of repeating D-galactose and 3,6-anhydro D-galactose units arranged in a linear fashion. The polymer is highly sulfated having three $SO_3$ groups per each disaccharide unit Carrageenan has a continuum of molecular weights. In general, the carrageenan mixtures for use in the compositions of the present invention may have a molecular weight of up to about $2\times10^6$ daltons with less than about 1% of carrageenan molecules having an average molecular weight of $1\times10^5$ daltons (as determined by gas permeation chromatography and light scattering). More particularly, a lambda carrageenan in the invention has a weight average molecular weight of about 600,000 to about 1,200,000 daltons. This physical property imparts non-absorbability to the final formulation that in turn provides prolonged anti-microbial activity.

The carrageenans of the present invention can provide several other benefits. They remain stable if exposed to freezing, ambient, or boiling temperatures. The mixture is compatible with the human vaginal environment. Without intending to be bound by any particular theory of operation, it is believed that the carrageenans are compatible with the human vaginal environment and do not act as a substrate or otherwise cause or stimulate growth of natural vaginal flora, nor are they toxic so as to disrupt the natural floral balance in the vagina. Aside from the properties attributable to the carrageenans of the present invention, their antimicrobial activity extends over a period of time because they are not systemically absorbed or degraded to any absorbable by-products detrimental to humans.

As discussed above, Applicants have previously reported the antiviral effects of a complex between a water-soluble metal salt and the carrageenans. Such complexes of metal salt and carrageenans may be employed in the compositions of the present invention in combination with one or more lectins. In preferred embodiments, the metal salt is a zinc salt (and the antimicrobial composition may be referred to as "zinc carrageenate").

Zinc is an inhibitor of such sexually transmitted pathogens as HIV and HSV-2. Zinc acetate and zinc sulfate have been shown to inhibit HIV infection in cell culture, and HSV-2 in both cell culture and laboratory animals. Zinc salts have been shown to be effective in blocking infection by HIV in vitro (Haraguchi, Y., et al. *Antiviral Res* 43, 123-133 (1999) and also blocking infection by foot-and-mouth virus, human rhinovirus, influenza A and B, semliki forest virus and sindbis virus (Sergio, W. *Medical Hypotheses* 26, 253 (1988)). Haraguchi, et al. found that zinc chloride, cadmium acetate and mercury chloride inhibited HIV-1 production as assayed by p24 ELISA and RT. Zinc chloride did not exhibit significant cytotoxicity when present in concentrations of up to 550 µg/mL. Additionally, Fenstermacher and DeStefano have proposed that zinc form a highly stable HIV reverse transcriptase-(primer-template) complex with profoundly diminished catalytic activity. Fenstermacher K J, Destefano J J. Journal of Biological Chemistry. 2011 Nov. 18; 286(47): 40433-42.

Thus, in addition to being used in combination with carrageenans and lectins, it is also contemplated herein that water-soluble zinc salts may be used in combination with one or more lectins in the compositions of the instant invention. Specifically, a composition comprising GFRT and zinc acetate may be used in combination to enhance the anti-HIV potency of GFRT.

Zinc salts useful in the present invention include both inorganic salts and organic salts that exhibit anti-microbial properties without causing unacceptable irritation when used in accordance with the present invention. Possible water-soluble zinc salts for use with the instant invention include zinc acetate, zinc propionate, zinc butyrate, zinc formate, zinc gluconate, zinc glycerate, zinc glycolate, zinc lactate, zinc sulfate, zinc chloride, and zinc bromide. Use of $ZnSO_4$, $ZnCl_2$, $ZnBr_2$, $Zn(Ac)_2$, etc. are also contemplated herein. Copper and silver counterpart salts are also useful in the present invention provided that they are non-irritating in vivo and do not cause degradation to any absorbable by-products detrimental to humans. As contemplated herein, the compositions of the instant invention may include between about 0.03% and 1.5% of water-soluble metal salts, and particularly from about 0.3% to 1.0% by weight of the total weight of the composition.

Complexes of carrageenan and a zinc metal, and particularly zinc acetate for use in the present invention may be prepared according to methods disclosed in the prior art, e.g., as described in U.S. Pat. No. 8,367,098. See also Fernandez-Romero J A, et al. Antimicrobial Agents and Chemotherapy. 2012 January; 56(1):358-68; Kenney, J., et al., Antimicrobial agents and chemotherapy, 2013. 57(8): p. 4001-9, all incorporated by reference herein. Briefly, such complexes may be prepared by standard processes whereby the metal ions replace cations that are naturally present on the backbone of the polysaccharide. For example, zinc carrageenan (which refers to a complex between zinc cations and the carrageenans of the present invention) is a compound synthesized by a procedure whereby zinc is non-covalently attached to the sulfate groups of the carrageenans. Kenney, J., et al., Antimicrobial agents and chemotherapy, 2013. 57(8): p. 4001-9.

The above procedures generate a compound which is water soluble and active against enveloped viruses such as HIV and HSV-2 or naked viruses like HPV. Unlike inorganic or simple organic zinc salts, zinc carrageenan maintains the preferred rheological properties and possesses a high molecular weight (up to 2,000,000 Da) making it amenable to be formulated into a vaginal or rectal product, which is non-irritating and not absorbed. The composition may be referred to as a "complex" due to the presence of molecular interactions between the metal and the carrageenans that disfavor or discourage its dissociation to free metal cations.

The present complexes of a metal salt and a negatively charged sulfated-polysaccharide complex are distinct from mixtures of water-soluble metal salts and carrageenans in terms of their physical, chemical and/or anti-microbial properties.

As disclosed herein, the addition of one or more lectins to a combination of a water soluble zinc metal salt and carrageenans; or a combination of a lectin with either a zinc metal salt or with carrageenans can provide compositions with enhanced anti-viral potency. Lectins suitable for use in the compositions of the instant invention include but are not limited to Griffithsin, Cyanovirin, Scytovirin, Actinohivin and other antiviral lectin proteins. See e.g., Brichacek B, et al., In Vivo Evaluation of Safety and Toxicity of a *Lactobacillus jensenii* Producing Modified Cyanovirin-N in a Rhesus Macaque Vaginal Challenge Model. Bereswill S, editor. PLoS ONE. 2013 Nov. 12; 8(11):e78817; Takebe Y, et al. Antiviral Lectins from Red and Blue-Green Algae Show Potent In Vitro and In Vivo Activity against Hepatitis C Virus. Choi J, editor. PLoS ONE. 2013 May 21; 8(5): e64449; Tanaka H, et al. Proceedings of the National Academy of Sciences. 2009 Sep. 15; 106(37):15633-8; and O'Keefe, B. R., et al., Proceedings of the National Academy of Sciences of the United States of America, 2009. 106(15): p. 6099-104.

Most particularly, Applicants have discovered that the addition of GFRT to compositions of carrageenan and compositions of zinc acetate (alone or in combination) can provide unexpected and synergistic anti-viral activity. Specifically, as provided in the below examples, the anti-HIV activity of GFRT is profoundly enhanced in the presence of zinc acetate. Also, the inhibitory activity of carrageenan on HPV, as well as the inhibitory effect of the combination of carrageenans and zinc acetate on HSV-2, are synergistically enhanced in the presence of GFRT.

Thus, as contemplated herein, the antimicrobial compositions of the present invention may particularly comprise one or more lectins in combination with one or more of a zinc metal and a carrageenan. These anti-microbial agents may be used in the various combinations recited herein to provide microbicidal compositions with enhanced and synergistic anti-microbial activity. Such compositions may be made according to conventional methods. For example, the additional agents, e.g., GFRT and/or ZA may be in admixture and/or associated with the carrageenans such as in the form of a complex. For example, the carrageenans may be in the form of a complex with a zinc metal such as disclosed in U.S. Pat. No. 8,367,098.

The combination of the carrageenans, the water soluble metal salts, and the lectins contemplated herein preferably include the carrageenans discussed above, including lambda carrageenan in amounts of at least about 50% by dry weight of the carrageenans with the remainder of the carrageenans being at least one non-lambda carrageenan, and most preferably a combination of 95% lambda carrageenan and 5% kappa carrageenan, with the overall composition in the form of a gel including between 1% and 5% carrageenan, preferably about 3% carrageenan; the compositions include the water-soluble metal salts preferably comprising zinc salts, most preferably in the form of zinc acetate or zinc lactate, including from about 0.1 wt. % and 1.5 wt. % of the metal, such as zinc, in the overall composition, most preferably about 0.3 wt. % thereof; and may further include one or more lectins. In a particular embodiment, the amount of lectins may be from between about 0.01 to 1%, and particularly from between about 0.05% to 0.2%, of the total weight of the composition. As contemplated herein, the lectin, e.g., GRFT, may be present in a composition such that it is 0.1% of the total weight of the composition.

As contemplated herein, an "effective amount" of an "antimicrobial agent" is an amount sufficient to inhibit the infectivity of one or more microbial infections in a subject in need thereof. As understood by one of skill in the art, however, the effective amount of the antimicrobial agent, or the actual weight percentage of such agent used in the compositions, can vary depending upon a variety of factors, including for example, the actual antimicrobial activity of the lectins and other antimicrobial agents in the composition towards the target microbes to be treated. Such activity can be determined according to conventional methods and the amount of active agents formulated accordingly. For example, anti-viral activity of a substance may be measured according to the methods described herein in FIG. 1 and Table 2. Other factors for consideration in determining a dosage amount of an active antimicrobial agent are familiar to one of skill in the art and include the actual dosage form and manner of delivery of a pharmaceutical composition, e.g., whether the dosage form is intended for extended release.

It is understood herein that the individual active antimicrobials in a composition, e.g., anti-viral components which make up the antimicrobial agent of the compositions of the instant invention each may be present in the composition in an amount sufficient to produce a microbicidal, e.g., antiviral effect upon administration of the composition to a subject in need thereof. As described herein, and detailed in the below examples, enhanced and synergistic microbicidal effects can be achieved upon combination of certain antiviral agents.

Thus, as discussed above, in order to provide an antimicrobial effect, the lambda carrageenan or the carrageenans are generally present in amounts of about 1 to about 5%, based on total weight of the composition. When included in a composition of the present invention, in preferred embodiments, the carrageenans are present in amount of about 3% by total weight of the composition. However, such amounts, as well as the amount of lectin, metal salts, and other agents may vary and be determined by one of skill in the art using conventional methods.

By "antimicrobial" or "antimicrobial effect", it is meant that the composition inhibits or reduces the likelihood of transmission of a sexually transmitted infection caused by a bacterium, protozoan, virus, or another microbe. The compositions of the present invention are useful in protection against sexually transmitted infections e.g., by inhibiting infection by HIV, HPV and HSV-2. On the other hand, the terms "antimicrobial" and "antimicrobial effect" are not meant to convey, imply or be limited to any particular means by which the inhibition of transmission of the infection is accomplished.

Applicant has also surprisingly discovered that GFRT has anti-viral effects on HPV. Thus, compositions comprising GFRT alone or in combination with other anti-microbial and pharmaceutical agents, as well as methods to treat HPV infections in a subject in need thereof by administering such compositions, are included in the present invention. The effective amount of GFRT in such compositions and dosage forms may be determined by one of skill in the art according to conventional methods, e.g. as discussed herein.

One of skill in the art will recognize that any one or more of the microbicidal compositions disclosed herein may also have inhibitory effect on other STIs, and thus administration of these compositions to a subject in need thereof may be used concurrently to treat or prevent infections by other STIs as part of a multipurpose prevention technology and thus achieve a public health benefit.

Thus, it is contemplated herein that the antimicrobial compositions of the present invention may be administered to a subject, such as a human, in order to treat or prevent a microbial infection, including but not limited to a viral infection, e.g., by inhibiting the growth or replication of a microbe. Viruses of particular interest for treatment and prevention include, but are not limited to various strains of HIV, HPV, HSV, including HSV-2.

As used herein, a subject in need thereof includes humans who are at risk of microbial, e.g. viral infection or who are already infected. As particularly contemplated herein, risk of microbial infection includes risk of viral infection and includes but is not limited to risk of infection by sexual transmission. As used herein, the term "treatment" of a subject is familiar to one of skill in the art and encompasses a reduction in the symptoms and/or pathogen shedding in an already infected individual. Such reduction may be associated with a decrease in the likelihood of transmission of the pathogen to another individual, and also a reduction in the likelihood of the treated subject acquiring another microbial infection, e.g., HIV. For example, it has been observed that an individual with a herpes infection has an increased propensity of acquiring HIV infection. Thus, it is believed that treatment of an STI according to the methods of the present invention will have the related benefit of making a patient less susceptible to other infections e.g., HIV.

As used herein, the term "prevention" is understood to refer to a prophylactic treatment designed to reduce the likelihood of a microbial infection, including but not limited to infection of a non-infected, susceptible individual through sexual transmission.

As used herein, "other STIs" are familiar to one of skill in the art and include, e.g., *N. gonorrhoeae, C. trachomatis*, bacterial vaginosis, *T. vaginalis*, Hepatitis B and others.

In addition to the carrageenans, lectins, and metal salts discussed herein, other antimicrobial compounds can also be used in the compositions of the present invention, including polymers such as naphthalene sulfonates and other sulfated or sulfonated polymers (McCormack S et al., Lancet. 2010 Oct. 16; 376(9749):1329-37; dendrimers (Rupp R, et al., Int J Nanomedicine, 2007; 2(4):561-6; and cellulose, including cellulose analogues and derivatives thereof (Chaobo Huang, et al., Biomaterials Volume 33, Issue 3, January 2012, Pages 962-969. These and other suitable antimicrobial agents, including but not limited to antiviral compounds suitable for use in the compositions of the instant invention are familiar to one of skill in the art.

The compositions of the instant invention may be formulated to further contain other active agents and/or inert ingredients, depending upon the intended use (as described below). For example, pharmaceutical formulations comprising one or more therapeutic agents including, e.g., one or more active antimicrobial agents or other therapeutic agent or drug in a pharmaceutically acceptable carrier are contemplated herein. Suitable carriers for use in the pharmaceutical compositions, and particularly for use with vaginally and rectally acceptable dosage forms of the compositions contemplated herein, are familiar to one of skill in the art and include, e.g., various commercially available physiologically acceptable vehicles, adjuvants, excipients, and diluents.

Such compositions may be formulated for prescription as well as over the counter use. As understood herein, an "over-the counter" pharmaceutical composition (also known as "OTC" or nonprescription medicine), is familiar to one of skill in the art and refers to a medicine that can be bought without a prescription.

In particular embodiments, compositions of the present invention may also contain a vaginally administrable drug. Preferred drugs include, e.g., contraceptive agents, such as steroid hormones, e.g., those disclosed in Saleh, et al., U.S. Pat. No. 5,972,372 ("Saleh"), the disclosure of which is hereby incorporated by reference. Examples of contraceptive agents useful in the present invention include progestins, ACTH, androgens, estrogens, gonadotropin, human growth hormone, menotropins, progesterone, progestins (e.g., levonorgestrel, norethindrone, 3-keto-desogestrel and gestodene), progestogen, urofollitropin, vasopressin and combinations thereof. Preferred agents include progestational compounds (e.g., norethindrone acetate and NESTORONE™ ("NES")). (i.e., 16-methylene-17.alpha.-acetoxy-19-norpregnene-3,20-dione)), and progestins (e.g., levonorgestrel (LNG)).

A preferred contraceptive agent is Nestorone 16-methylene-17α-acetoxy-19-norpregn-4-ene-3, 20-dione (hereinafter "NES"), which has been identified in the literature as "ST-1435". In comparative studies using the classic bioassay of measuring progestational potency, NES was found to have progestational activity 100 times higher than that of progesterone and 10 times higher than that of levonorgestrel. Kumar, N., et al. *Steroid* 65, 629-636 (2000)). Therefore, smaller amounts of NES are required to achieve ovulation inhibition. This potency combined with a lack of androgenic, estrogenic and glucocorticoid-like (hepatic glycogen deposition) activity and the lack of effects on lipid or clinical chemistry parameters, confer special advantages for the use of NES in contraceptives. Kumar, N., et al. Steroid 65, 629-636 (2000); Odlind, V., et al. Contraception 31, 130 (1985); Robins, A. & Bardin, C. Ann N Y Acad Sci 828, 38-46 (1997). However, NES has been shown to undergo rapid metabolism and inactivation upon oral administration making it suitable for use in nursing women when given via implants or vaginal rings. Massai, R., et al. Steroid 65, 703-707 (2000); Lahteenmaki P L A, et al. Contraception 42, 555-562 (1990)). A preferred delivery dose of NES when combined with the K/λ carrageenan mixture in gel form is between about 75 and about 100 μg per day, which will reach plasma levels of NES around 200 pmol/L and achieve good bleeding patterns during menses. Other preferred vaginally administrable drugs include agents for hormone replacement therapy such as estrogenic substances (e.g., ethynylestradiol) and other steroidal compounds.

Without intending to be bound by any particular theory of operation, it is believed that the carrageenans possess a dual function of imparting microbicidal properties while providing a release delivery system for a contraceptive agent or agent for hormone replacement therapy. In addition, it is believed that the carrageenans can impart microbicidal properties while stabilizing protein emulsions. While they may be used in the compositions in the form of a gel, the compositions described herein are not limited to only comprising the use of carrageenan gels. Formulations for other delivery systems can be prepared, and thus the compositions may be in any physical form suitable for delivery of the antimicrobial agents, including as a gel, or in solution, or as a solid, or in dried or powdered forms.

The composition may further contain a physiologically acceptable pH controlling agent suitable for use with the compositions disclosed herein. Suitable buffer agents may be determined by one of skill in the art using conventional methods. In a particular embodiment the buffer is an acetate buffer. In a further embodiment, the acetate buffer comprises a mixture of acetic acid and sodium acetate.

In a particular embodiment, the compositions may further comprise a preservative. In a particular embodiment the preservative is methyl paraben. Other suitable preservatives include, e.g. alkyl esters of para-hydroxybenzoic acid, such as methyl paraoxybenzoate, propyl paraoxybenzoate, hydantoin derivatives, parabens, such as methyl paraben, propioniate salts, triclosan tricarbanilide, tea tree oil, alcohols, farnesol, farnesol acetate, hexachlorophene and quaternary ammonium salts, such as benzolconjure, zinc and aluminum salts, sodium benzoate, benzyl alcohol, benzalkonium chloride and chlorobutanol. In general, the preservative is present in an amount up to about 0.3% based on the total weight of the composition.

In addition to inhibiting the growth of microorganisms that may be introduced inadvertently during manufacturing, the preservative can prevent any deleterious effects that might occur to the active agents in the composition due to the presence of normal body flora once the composition is introduced into the body. This will prolong the length of time that the active agents in the composition remain active. The compositions include from about 5 mM to about 25 mM of the pH-controlling agent and 0.1% to 0.3% preservative.

The compositions of the present invention may be administered in various dosage forms familiar to one of skill in the art as contemplated according to the methods of the present invention. Thus, it is understood herein that the pharmaceutical formulations of the antimicrobial compositions of the present invention include conventional formulations suitable for use with dosage forms and routes of administration appropriate for treatment using the antimicrobial agents disclosed herein. Such formulations can include, e.g., liquid solutions, liquid suspensions, tablets, capsules, gelcaps, aerosols, and transdermal patches comprising an effective amount of one or more antimicrobial agents for oral, nasal, and/or topical administration. Thus, it is contemplated herein that the compositions may be administered to treat or prevent a systemic infection. However, as contemplated herein, in particular embodiments, the pharmaceutical formulations and compositions of the present invention are intended for vaginal and/or rectal administration to prevent or treat infection.

Such compositions may be suitably formulated e.g., into gels, creams, foams, films, tablets and suppositories, intravaginal rings, intrauterine devices or systems and nanofibers by one of skill in the art in accordance with standard techniques in the pharmaceutical industry.

As contemplated herein, the methods of the present invention comprise administering the compositions disclosed herein according to a mode and frequency of administration designed by one of skill in the art to achieve administration of a therapeutic dosage in an amount and over a period of time that is best suited to prevent or treat a microbial infection in a subject in need thereof. Such administration may be, e.g., for immediate or extended release.

The following examples are intended to further illustrate certain embodiments of the invention and are not intended to limit the invention in any way. Conventional methods and commercially available reagents are utilized in the experiments described herein below, with the exception of GFRT which was kindly provided by B. O'Keefe (Molecular Targets Development Program, National Cancer Institute at Frederick, Frederick, Md.).

Example 1. Production of a GZC Gel Formulation

A method for the preparation of a combination of carrageenans+zinc acetate suitable for use in the instant invention has been previously described, and is summarized hereinbelow. See, e.g., Kenney J, et al. Antimicrobial Agents and Chemotherapy. 2013 Jul. 15; 57(8):4001-9.

Production of carrageenan: For step 1, a 4-liter double planetary mixer (Charles Ross & Son, Hauppauge, N.Y.) was charged with 2,829 g of sterile filtered water and 3.923 g of sodium acetate trihydrate (Sigma). The solution was heated for 5 min at 69° C. with stirring at 40 rpm. Carrageenan (102 g, 3.4% final concentration) was added, and the mixture was stirred for 3 h at 69° C. For step 2, after the formulation was cooled to 25° C., a solution of 6 g of methyl paraben (Spectrum, Gardena, Calif.)-60 ml of propylene glycol (Sigma) was added, and the solution was stirred for an additional 1 h at 40 rpm. The formulation pH was adjusted to 6.8, and the reaction volume was stirred for 15 min under vacuum conditions to remove bubbles.

Production of Zinc Acetate/Carrageenan: For step 1, a protocol similar to that used to make Carrageenan was used to generate a combination of zinc acetate/carrageenan with the following changes: 894 ml of 10 mM sodium acetate buffer (pH 6.4) was used. Carrageenan (31 g) was added to reach a final concentration of 3%. A solution of 3 g zinc acetate dihydrate-50 ml sodium acetate buffer was added, and the solution was stirred for an additional 20 min at 40 rpm. A mixture of 2 g methyl paraben-20 ml propylene glycol was used.

Methyl paraben content, zinc content, and physiochemical properties (osmolality, pH, simple viscosity) were determined using established methods such as described in Fernandez-Romero J A et al., 2012, Antimicrob Agents Chemother. 56:358-368.

Stability studies. Aliquots (25 g) of gel were stored in 30-ml polypropylene bottles (Qorpak, Bridgeville, Pa.) under the following conditions: 30° C./65% relative humidity (RH), 40° C./75% RH, and 50° C./ambient humidity. Bottles were removed periodically, and the gel was analyzed for methyl paraben content, osmolality, pH, viscosity, and zinc content, e.g., as described in Fernandez-Romero J A et al., 2012, Antimicrob Agents Chemother. 56:358-368.

Production of Griffithsin/Zinc Acetate/Carrageenan Formulation: The procedure for preparing a zinc acetate/carrageenan formulation provided above are repeated as provided above with the addition of third step wherein an aqueous solution of GRFT is added to the zinc acetate/carrageenan formulation (O'Keefe, B. R., et al., Proceedings of the National Academy of Sciences of the United States of America, 2009. 106(15): p. 6099-104; U.S. Pat. No. 8,088, 729) and mixed as in step 2 for an additional 20 minutes at 40 rpm at 25 C.

Example 2. Activity of GRFT Against HIV and HPV in In Vitro Assays

The activity of GRFT against HIV was verified in standard in vitro assays. Briefly, GRFT was provided by Dr. Barry O'Keefe (NCI) and its anti-HIV activity was tested in TZM-bl cells (NIH AIDS Research and Reference Reagent Program) using the MAGI assay e.g., as described in Begay O, et al. AIDS Research and Human Retroviruses. 2011 Sep. 1; 27(9):1019-24 and the laboratory strains HIV-1$_{MN}$ (X4 virus) and HIV-1$_{ADA-M}$ (R5 virus); see FIG. 1A.

The laboratory strains HIV-1$_{MN}$ (X4 virus) and HIV-1$_{ADA-M}$ (R5 virus) were provided by Dr. J. D. Lifson at the AIDS and Cancer Virus Program, SAIC-Frederick, Inc., National Cancer Institute, Frederick, Md. TZM-bl cells were treated with different non-toxic GRFT concentrations immediately before adding HIV-1 viruses (100-200 infectious units) followed by 72 h incubation before fixing and staining the cell monolayers. The $IC_{50}$ values (showed in graph as a vertical dotted line with the 95% confidence interval) were calculated using a dose-response-inhibition analysis on GraphPad Prism v5.0 software. All the non-toxic GRFT concentrations were tested in triplicates. The graphics show the mean±SD.

Anti-HIV activity was also tested in peripheral blood mononucleated cells (PBMC) using the laboratory strains HIV-$1_{NL4-3}$ according to conventional methods. See Trkola A, et al., J Virol. 1999 November; 73(11):8966-74. Briefly, activated PBMCs ($2 \times 10^6$/ml) were treated with different non-toxic concentrations of GRFT before adding 100 $TCID_{50}$ of virus followed by an overnight incubation. The supernatant was replaced with fresh stimulation media on days 1 and 4 post infection. The p24 level in the supernatant was tested on day 7 after infection using the p24 ELISA. The $IC_{50}$ values (showed in graph as a vertical dotted line with the 95% confidence interval) were calculated using a dose-response-inhibition analysis on GraphPad Prism v5.0 software. All the non-toxic GRFT concentrations were tested in triplicates. See FIG. 1B. The graphics show the mean±SD. Data from both assays confirmed that GRFT possesses potent anti-HIV activity in vitro.

The activity of GRFT against HPV pseudoviruses was also investigated. Specifically, anti-viral activity of GRFT on HPV16, HPV18 and HPV45 pseudovirus (PsV) activity was estimated using the Luciferase assay in HeLa cells (Buck C B, et al. PLoS Pathog. 2006 Jul. 1; 2(7):e69.) In this experiment, Hela cells were treated with different non-toxic GRFT concentrations immediately before adding HPV16, HPV 18 or HPV45 PsV (an amount of virus that produce ~300-700 relative luminescent units) followed by 72 h incubation. The luciferase assay was performed to obtain a dose-response curve shown in FIG. 1C. The $IC_{50}$ values (showed in graph as a vertical dotted line with the 95% confidence interval) were calculated using a dose-response-inhibition analysis on GraphPad Prism v5.0 software. All the non-toxic GRFT concentrations were tested in triplicates. The graphics show the mean±SD. The data indicate that GRFT has moderate in vitro activity against HPV16, 18, and 45 PsVs.

Example 3. GRFT Combination with ZA and C Results in Anti-HIV and Anti-HPV Synergy The anti-HIV and anti-HPV activity of GRFT in combination with zinc acetate (ZA) and carrageenan (C) was tested according to the methods described above. Briefly, in order to test anti-HIV activity, activated PBMCs were treated with varying equipotent doses (based on $IC_{50}$ of each API) of GRFT, ZA or GRFT+ZA at 37° C. 1 h prior to exposure to 100 $TCID_{50}$ of HIV-$1_{92BR014}$ in the presence of the same doses of each compound or combination (triplicates). Medium-treated (virus only) cells were included as a control. Eighteen hours later the cells were washed and plated in the presence of medium with IL-2 (with the only exception of those samples treated with ZA, where ZA was replaced). This step was repeated on day 4 and the supernatants collected on day 7 to measured HIV-1 p24 levels by ELISA. In order to assay for anti-HPV activity, HeLa cells were treated with varying equipotent doses of GRFT, C or GRFT+C (based on $IC_{50}$ of each API) at 37° C. and immediately exposed to HPV16 PsV (triplicates). Medium-treated (virus only) cells were included as a control. The luciferase assay was performed 72 h after infection. Combination indexes (CI) were estimated using the Chou-Talalay method (Chou, T. C. Pharmacological Reviews, 2006, 58(3): p. 621-81) with the Cacusyn for Windows software (Biosoft, Cambridge, United Kingdom). Results are provided in Table 1. As provided therein, "CI" refers to a quantitative measure of the degree of drug interaction as follows: additive effect (CI=1); synergism (CI<1), or antagonism (CI>1). "Dm" refers to the median-effect dose ($IC_{50}$); "m" refers to a measurement of the sigmoidicity of the dose-effect curve, and also represents the slope of the median-effect plot; and "r" refers to the linear correlation coefficient of the median-effect plot. As used therein, % $IC_{50}$ reduction=1-[$IC_{50}$ combination/$IC_{50}$ GRFT]*100. ¶ % $IC_{50}$ reduction values are based on API with bold font. N/A=Not applicable.

Data provided in Table 1 indicate that there is a surprising synergy between ZA and GRFT against HIV and also between C and GRFT against HPV16 PsV (Table 1; CI values less than 1). In addition, importantly, no evidence of antagonism between GRFT and C or ZA is seen.

TABLE 1

GRFT combination with ZA and CG results in anti-HIV and anti-HPV synergy.

| Drug (µM) | CI | | | | | | % $IC_{50}$ reduction¶ |
|---|---|---|---|---|---|---|---|
| | $ED_{50}$ | $ED_{75}$ | $ED_{90}$ | Dm | m | r | |
| Anti-HIV combination activity^ | | | | | | | |
| GRFT | N/A | N/A | N/A | 0.0004 | 2.784 | 0.958 | N/A |
| ZA | N/A | N/A | N/A | 48.3 | 2.655 | 0.945 | N/A |
| GRFT + ZA | 0.500 | 0.494 | 0.489 | 0.0002 | 2.866 | 0.827 | 50 |
| Anti-HPV combination activity* | | | | | | | |
| C | N/A | N/A | N/A | 0.052 | 1.058 | 0.966 | N/A |
| GRFT | N/A | N/A | N/A | 32.7 | 1.029 | 0.878 | N/A |
| C + GRFT | 0.523 | 0.548 | 0.575 | 0.010 | 0.995 | 0.964 | 80.8 |

Example 4. GRFT Prevents HSV-2 Entry to Target Cells but not Viral Adsorption

Figure 2:
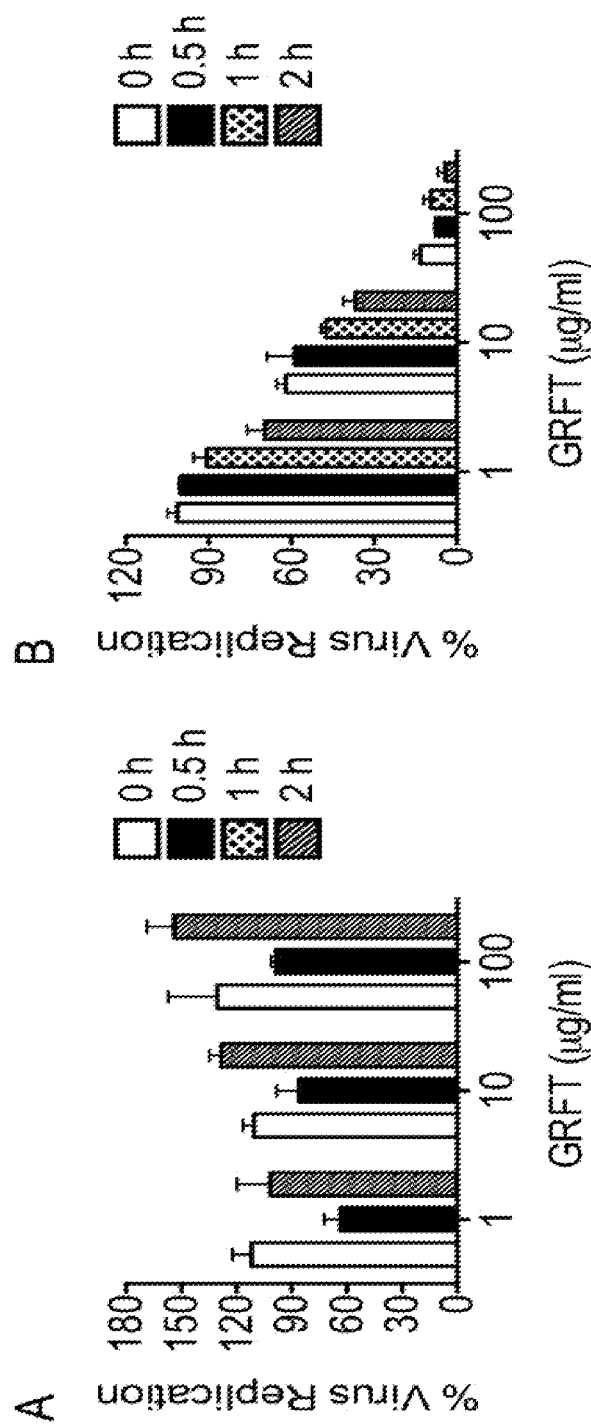
FIG. 2 depicts bar graphs which illustrate that GRFT prevents HSV-2 entry to target cells but does not prevent viral adsorption.

A recent study from Nixon et al. (Nixon, B., et al., Journal of virology, 2013. 87(11): p. 6257-69) showed that GRFT blocks HSV-2 infection in vitro and in vivo and proposed the inhibition of the virus cell-to-cell spread as the mode of action. We have performed experiments in Vero cells that suggest an inhibition of HSV-2 entry but not adsorption to target cells. For inhibition of virus adsorption, the plaque inhibition assay was performed as previously described. Ashley, R., Herpes simplex viruses, p 375-395. In Schmidt N.J., Emmons R W (ed), Diagnostic procedures for viral, rickettsial, and chlamydial infections, 7th ed. American Public Health Association, Washington, D.C. 1995. Briefly, HSV-2 G strain and different concentrations of GRFT or media (virus control) were pre-incubated for 0, 0.5, 1 and 2 h at 37° C. before adding to pre-chilled Vero cells and kept at 4° C. The monolayers were washed three times with cold media before adding a methylcellulose overlay and incubated for 48 h at 37° C., 5% $CO_2$ and 98% humidity before fixing, staining and counting the plaque forming units (pfu). The % of virus replication was calculated versus the virus control. See FIG. 2 A. Inhibition of virus entry was also assayed. Briefly, the same assay was performed as in the adsorption study described above and in FIG. 2A, however, after the 2 h incubation at 4° C., the cells were switched to 37° C., 5% $CO_2$ and 98% humidity for an additional 2 h. The monolayers were treated for 2 minutes with citric acid buffer (pH=3.0) to inactivate any virus remaining on the cell surface. The monolayers were washed three times with cold media before adding a methylcellulose overlay and incubated for 48 h at 37° C., 5% $CO_2$ and 98% humidity before fixing, staining and counting the plaque forming units (pfu). The graph depicted in FIG. 2B shows % of virus replication (mean±SD) relative to virus control (triplicates per condition).

Example 5. GRFT/ZA/C Combinations Increase the Antiviral Activity Against HSV-2

We previously reported that the combination of ZA and CG results in a potent antiviral synergy against HSV-2. Fernandez-Romero, J. A., et al., Antimicrobial agents and chemotherapy, 2012. 56(1): p. 358-68. More recently we explored the compatibility of GRFT, ZA and C at the level of in vitro anti-HSV-2 activity and have found that there is a profound reduction of $IC_{50}$ values when two or three of these compounds are combined. Briefly, HSV-2 G strain and different concentrations of each compound or their combinations (based on equipotency $IC_{50}$ ratios) were pre-incubated at 37° C. and added to Vero cells followed by a 6 day incubation at 37° C., 5% $CO_2$ and 98% humidity. A dye-uptake PrestoBlue assay was performed to test antiviral activity. Relative fluorescent units (RFU) were measured at 570 nm for excitation and 600 nm for emission. The % of virus replication was calculated using the following formula: % Virus replication=$[(O.D_{cell\ control}-O.D_{compound})/(O.D_{cell\ control}-O.D_{virus\ control})]*100$. $IC_{50}$ values were calculated using a dose-response-inhibition analysis on GraphPad Prism v5.0 software. Data are provided herein below in Table 2. As provided therein, ¶ $IC_{50}$ or % $IC_{50}$ reduction values are based on API with bold font; NA=Not applicable.

TABLE 2

GRFT/ZA/C combinations increase the antiviral activity against HSV-2.

| API combinations | $IC_{50}$¶ (95% confidence interval) | % $IC_{50}$ reduction¶ |
|---|---|---|
| GRFT | 19 µg/ml (16.1 to 22.4) | N/A |
| ZA | 58.2 µg/ml (43.0 to 78.8) | N/A |
| C | 11.5 ng/ml (9.7 to 13.6) | N/A |
| C + GRFT | 3.4 ng/ml (2.3 to 4.9) | 70.4 |
| C + ZA | 1.9 ng/ml (1.6 to 2.4) | 83.5 |
| GRFT + ZA | 2.5 µg/ml (2.2 to 2.9) | 86.9 |
| C + GRFT + ZA | 1.7 ng/ml (1.2 to 2.2) | 85.2 |

Example 6. GZC Significantly Reduces HSV-2 Infection in a Stringent Mouse Model

In order to determine if the GZC combination was effective against HSV-2 in vivo, we used the highly stringent model in which DepoProvera treated mice are treated with zinc acetate/carrageenan gels 1 or 2 hours prior to vaginal challenge with $10^6$ pfu HSV-2. Fernandez-Romero JA, et al. Antimicrobial Agents and Chemotherapy. 2012 January; 56(1):358-68.

Briefly, Depo-treated Balb/C mice were challenged with $10^6$ pfu HSV-2 1 (FIG. 3A) or 2 (FIG. 3B) hours after the indicated formulations (GZC=GRFT+ZA+C; ZC=ZA+C; GC=GRFT+C and where C in this example refers to a carrageen. All the formulation in this example were applied as gel formulations (n=15-30/formulation). The percentages of uninfected animals over time, based on symptoms, were recorded and are shown for each treatment group in FIG. 3.

Figure 3:
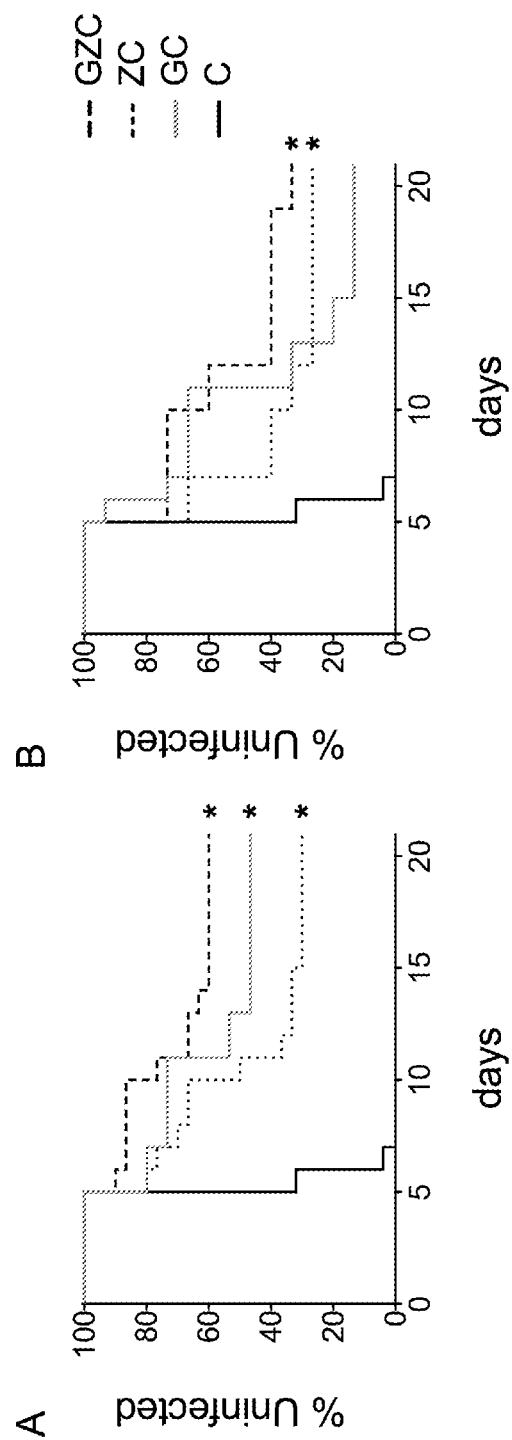
FIG. 3 is a graph which depicts that a microbicidal composition comprising GZC significantly reduces HSV-2 infection in a stringent mouse model. Depo-treated Balb/C mice were challenged with 106 pfu HSV-2 1 (A) or 2 (B) hours after the indicated formulations (GZC=GRFT+ZA+CG; ZC=ZA+CG; GC=GRFT+CG and C=CG, i.e., a carrageenan gel) were applied (n=15-30/formulation). The percentages of uninfected animals over time, based on symptoms, are shown for each treatment group. Significant difference between the combination formulations and C alone is indicated by the asterisks (p<0.037). There was also significant difference between GZC vs. ZC (p=x) and GC vs. ZC (p=X) at 1 hour and between GZC vs. GC (p=X) and ZC vs. GC (p=X) at 2 h. The statistical analysis was performed using the Fisher's exact test.

Significant difference between the combination formulations and C alone is indicated by the asterisks (p<0.037). The statistical analysis was performed using the Fisher's exact test. Using this approach, we found that a composition comprising 0.1% GRFT, 0.3% ZA and 3% CG gel (GZC) significantly reduced HSV-2 infection (relative to the CG control; FIG. 3). Notably, the infection frequency in GZC-treated mice was lower than that seen in the GC or ZC groups.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An antimicrobial composition comprising Griffithsin in an amount of from about 0.01% to 1% by total weight of the composition; and
    an agent selected from the group consisting of: a physiologically acceptable water soluble metal salt in an amount of from about 0.03% to about 1.5% based on the total weight of the composition, carrageenan in an amount of from about 1% to about 5% by total weight of the composition, and combinations thereof.

2. The antimicrobial composition of claim 1 further comprising an acetate buffer, wherein the acetate buffer comprises a mixture of acetic acid and sodium acetate.

3. The antimicrobial composition of claim 1 further comprising a physiologically acceptable preservative.

4. The antimicrobial composition of claim 3 wherein said physiologically acceptable preservative comprises methyl paraben.

5. The antimicrobial composition of claim 1 wherein the composition comprises the metal salt in an amount of from about 0.3% to about 1% by total weight of the composition and carrageenan in an amount of from about 1% to about 5% by total weight of the composition.

6. The antimicrobial composition of claim 1 having a pH of about 5.5 to about 7.5.

7. The antimicrobial composition of claim 1 wherein said agent is zinc acetate.

8. The antimicrobial composition of claim 1 wherein the agent is a carrageenan.

9. The antimicrobial composition of claim 1 wherein said agent is zinc acetate and a carrageenan.

10. The antimicrobial composition of claim 1 further comprising a contraceptive agent.

11. The antimicrobial composition of claim 1 wherein said composition is in a dosage form selected from the group consisting of gels, creams, foams, films, tablets, suppositories, intravaginal rings, intrauterine devices or systems, and nanofibers.

12. An antimicrobial composition comprising:
    Griffithsin in an amount of 0.01% to 1.0% by weight of the composition;
    zinc acetate in an amount of from about 0.03% to about 1.5% based on the total weight of said composition; and
    carrageenan in an amount of from about 1% to about 5% by total weight of said composition.

13. The antimicrobial composition of claim 12 further comprising a contraceptive agent.

14. The antimicrobial composition of claim 12 wherein said composition is in a dosage form selected from the group consisting of gels, creams, foams, films, tablets, suppositories, intravaginal rings, intrauterine devices or systems, and nanofibers.

15. The antimicrobial composition of claim 12, further comprising methyl paraben.

* * * * *